United States Patent
Seibt

(10) Patent No.: US 8,729,505 B2
(45) Date of Patent: May 20, 2014

(54) METHODS AND APPARATUS FOR MONITORING HYGIENIC CONDITIONS ON BOARD A VEHICLE

(75) Inventor: Christian Seibt, Buchholz (DE)

(73) Assignee: Airbus Operations GmbH, Hamburg (DE)

(*) Notice: Subject to any disclaimer, the term of this patent is extended or adjusted under 35 U.S.C. 154(b) by 89 days.

(21) Appl. No.: 13/404,045

(22) Filed: Feb. 24, 2012

(65) Prior Publication Data

US 2012/0221192 A1 Aug. 30, 2012

Related U.S. Application Data

(60) Provisional application No. 61/446,232, filed on Feb. 24, 2011.

(30) Foreign Application Priority Data

Feb. 24, 2011 (DE) .......................... 10 2011 012 281

(51) Int. Cl.
*G01N 21/64* (2006.01)

(52) U.S. Cl.
USPC ....................................... 250/461.1

(58) Field of Classification Search
USPC ....................................... 250/461.1
See application file for complete search history.

(56) References Cited

U.S. PATENT DOCUMENTS

| 5,716,026 | A | 2/1998 | Pascasio et al. |
| 7,055,183 | B2 | 6/2006 | Hoehne et al. |
| 2003/0164456 | A1 | 9/2003 | Petrich et al. |
| 2003/0197122 | A1 | 10/2003 | Faiola et al. |
| 2009/0095906 | A1* | 4/2009 | Gavner et al. .............. 250/338.1 |
| 2009/0223635 | A1 | 9/2009 | Lawless |
| 2010/0168907 | A1 | 7/2010 | Valerio |
| 2011/0117025 | A1 | 5/2011 | Dacosta et al. |

FOREIGN PATENT DOCUMENTS

| DE | 2657851 A1 | 6/1978 |
| DE | 19838448 A1 | 4/2000 |
| DE | 10259997 A1 | 7/2004 |
| WO | 03073080 A1 | 9/2003 |

OTHER PUBLICATIONS

German Patent Office, German Office Action dated Oct. 21, 2011 for German Patent Application No. 102011012281.8.
European Patent Office, Extended European Search Report dated May 21, 2012 for European Application No. 12155136.0.

* cited by examiner

*Primary Examiner* — Kiho Kim
(74) *Attorney, Agent, or Firm* — Ingrassia Fisher & Lorenz P.C.

(57) ABSTRACT

An inspection device is provided to monitor hygienic conditions of a space unit for a vehicle. The vehicle includes, but is not limited to, an inspection device, the use of an inspection device, and a method to assure hygienic conditions in a vehicle. In order to optimize assuring hygienic conditions in interior spaces on board a vehicle an inspection device is provided that includes, but is not limited to, an optical detection device. The optical detection device generates electromagnetic radiation to irradiate a surface to be cleaned, and renders visible soiling that, in visible light, is invisible to the human eye. The optical detection device is permanently installable on an interior lining.

16 Claims, 10 Drawing Sheets

US 8,729,505 B2

METHODS AND APPARATUS FOR MONITORING HYGIENIC CONDITIONS ON BOARD A VEHICLE

CROSS-REFERENCE TO RELATED APPLICATIONS

This application claims priority to German Patent Application No. 10 2011 012 281.8 filed Feb. 24, 2011 and also claims priority to U.S. Provisional Patent Application No. 61/446,232 filed Feb. 24, 2011, which are all incorporated herein in their entirety by reference.

TECHNICAL FIELD

The technical field relates to hygiene on board a vehicle, in particular to an inspection device to assure hygienic conditions in interior spaces on board a vehicle. The technical field also relates to a vehicle comprising an inspection device to assure hygienic conditions, to the use of an inspection device, and to a method to assure hygienic conditions in a vehicle.

BACKGROUND

In order to provide an adequate level of hygiene and cleanliness on board a vehicle, such as aircrafts, busses or coaches, ships or trains, the interior spaces are cleaned at regular intervals, for example in case of aircrafts during the so-called turnaround periods, i.e., the periods in which the aircraft is situated on the ground between flight times. Similar is the case for trains which are cleaned, for example, during short night periods when not in use, or sometimes even during the journey. For economic reasons the turnaround times are preferably as short as possible, i.e., the period available for cleaning becomes increasingly shorter. At the same time the required level of user comfort rises increasingly, including in recent times more demanding hygiene requirements, above all in the context of the prevention of pandemics as they can, for example, be caused by influenza viruses. DE 102 59 997 A1 describes, for example, a method for cleaning and disinfecting toilets on board an aircraft.

Therefore, there is at least a demand to optimize assuring hygienic conditions in interior spaces on board a vehicle. In addition, other demands, desirable features and characteristics will become apparent from the subsequent summary and detailed description, and the appended claims, taken in conjunction with the accompanying drawings and this background.

SUMMARY

An inspection device is provided to assure hygienic conditions in interior spaces on board a vehicle. An inspection device or a space unit on board a vehicle may also be provided, as well as a method to assure hygienic conditions in a vehicle.

The term "vehicle" relates to aircrafts, trains, and ships, such as passenger boats and ferries, busses, or other transportation means. At this stage, it should be understood that this description uses the term "aircraft", which includes, in particular, airplanes and helicopters as well as airships.

According to a first embodiment, an inspection device is provided to assure hygienic conditions in interior spaces on board a vehicle, which inspection device comprises an optical detection device that generates electromagnetic radiation to irradiate a surface to be cleaned, which electromagnetic radiator renders visible such soiling that in visible light is invisible to the human eye. The optical detection device is permanently installable inside the vehicle.

The above assures that it is possible to render visible also soiling that with the human eye is invisible to cleaning personnel. This makes it possible on the one hand to detect any soiling that may still be in place during the cleaning process as well as cleaning soiled surfaces that can produce an increased odor nuisance, and on the other hand makes it possible to inspect that the area has been cleaned impeccably. Consequently, the quality of the cleaning is improved, and thus the required level of hygiene is assured. Since the detection device is to be permanently installed on the interior wall lining or interior ceiling lining, it is furthermore assured that rendering the area visible, and above all carrying out an inspection, can take place at any time. Furthermore, this means that time can be saved both during the cleaning process itself and during inspection because access to the inspection device is provided at any time.

Instead of, or in addition, to mounting the inspection device to a wall or ceiling structure, it is also provided to mount the detector device to permanently installed equipment or fixedly mounted furniture, or other permanent structures. Access to the inspection device can be limited to a defined circle of users, e.g. access permitted to cleaning personnel and crew. In this arrangement, the quality of cleaning is divided into the areas of cleanliness and hygiene. The term "cleanliness" covers, for example, visible cleanliness and the aspect of odor nuisance. The term "hygiene" covers, for example, any possible danger to the health of users.

According to an embodiment, the optical detection device comprises at least one UV-light source, i.e., a light source that generates ultraviolet light, and therewith irradiates the surface to be cleaned or to be inspected. For example, the optical detection device comprises a light source that highlights soiled areas. For example, the optical detection device comprises a light source that is especially designed to render urine visible.

According to another embodiment, a space unit for a vehicle, such as an aircraft, a bus, a train or a ship and the like, is provided that comprises an interior lining and an inspection device. The interior lining comprises a floor region and a wall lining that at least in part encloses an interior space. The inspection device is designed according to any of the described embodiments, and is permanently installed and arranged in such a manner that at least part of the floor region is temporarily irradiated by the optical detection device to render visible any soiling on the floor region that, in visible light, is invisible to the human eye.

According to a further embodiment, the inspection device is arranged such that a part of the wall lining is temporarily irradiated by the optical detection device to render visible any soiling on the wall lining that, in visible light, is invisible to the human eye. For example, the relevant components, e.g., the components or areas that according to experience are most prone to soiling, can be irradiated by the detection device.

The space unit can be a cabin space of an aircraft, an interior space in a railway carriage such as a cabin or passenger compartment, a salon coach or a service room, a passenger area or cabin in a bus, or similar areas, zones or cabins on board a ship or other kind of vehicle. Such spaces are at least partly enclosed by wall areas, usually covered with interior lining. However, also in case the outer body is directly visible inside, that surface is referred to as interior lining or wall lining. Of course, wall lining also refers to lining above, e.g., ceiling lining. However, those surfaces are usually not contaminated with soiling and are typically not surfaces to be cleaned.

Preferably, the inspection device is integrated in the interior lining. For example, the optical detection device can be designed to be integrated in an illumination device for the interior space. For example, the interior lining can comprise a ceiling region, and the optical detection device is arranged in the ceiling region. According to a further example, the optical detection device can also be arranged in the region of lining elements and in the region of installations to be arranged in closer proximity to surfaces to be irradiated, i.e., surfaces to be cleaned and inspected. For example, the space unit is designed as the cabin space with a seating arrangement.

According to an embodiment, the space unit is designed as a toilet unit, e.g., a toilet monument in an aircraft, a toilet compartment in a train and the like, and the interior space is a toilet space with a toilet facility. The inspection device is designed in such a manner that at least part of the floor region and/or the wall lining and/or the toilet facility can be irradiated by the optical detection device.

The term "toilet monument" relates, for example, to installations in a cabin region of an aircraft, which installations provide a separate space that is used as a toilet. A monument can, for example, be freely arranged within a cabin space, be designed in combination with other, smaller, space units to form a larger monument, or be arranged in lateral regions or edge regions of the cabin space. For example, the optical detection device is invisible to the user using the toilet facility. For example, the toilet facility comprises a toilet bowl. The toilet facility can also comprise one or several urinals. For example, the term "toilet facility" also comprises other components that are provided in the region of the cabin of the vehicle, such as an aircraft, a bus, a train or a ship and the like, for user comfort, which components are generally referred to as cabin consumer equipment. This relates in particular to a shower, urinal, bidet, washbasin, etc. The embodiments also relate to critical regions, e.g., in particular those regions which, due to confined spatial conditions, are prone to soiling, for example, to a diaper-changing table arranged directly above the toilet, to a washbasin arranged directly beside a urinal or a toilet.

The inspection device can, for example, be controlled, i.e., for example activated and deactivated, from outside the space unit, i.e., in the case of a toilet monument from outside the toilet space unit. Preferably, in case of aircrafts, the inspection device can be controlled by way of a flight attendant panel (FAP).

According to a further embodiment, the inspection device comprises an optical sensor for detecting electromagnetic radiation of a defined wavelength range, which radiation is reflected, depending on the soiling, by the floor and/or wall surface to be cleaned. Furthermore, the sensor is designed to generate a corresponding (measuring) signal. For example, a camera is provided as a sensor, which camera is connected to an evaluation unit for image evaluation in order to make it possible to spatially allocate soiling that has not yet been removed. In this arrangement, the camera detects the soiling rendered visible to the camera by the inspection device. Spatial allocation makes it possible to identify those areas that are still (by the human eye invisibly) soiled and that therefore require additional cleaning. In this arrangement, the inspection device and the camera can be designed in such a manner that soiling is visible to the camera. The spatial allocation makes it possible to carry out targeted renewed cleaning.

According to an exemplary embodiment, a camera, an evaluation unit and marking means are provided. The camera detects light of a defined wavelength range reflected from the surface to be cleaned. The evaluation unit is designed in such a manner that, by image evaluation, soiling that has not yet been removed can be spatially allocated. The marking means are designed in such a manner that any soiling not yet removed can be highlighted by visible marking. For example, it is also possible for an odor sensor to be provided that detects unpleasant odours, e.g., originating from urine. The signal of the odor sensor can be incorporated in data processing. In this manner a differentiation can take place between soiling and actual odor, which in turn can also be visually displayed by way of a display, e.g. on the flight attendant panel. The odor sensor, for example, is arranged in the air conditioning system of a toilet space.

According to a further embodiment, the inspection device comprises a query device for detecting an occupation status of a space unit on board a vehicle, such as an aircraft, a bus, a train or a ship and the like, and a control unit. Further, the control unit is designed in such a manner that the light radiation of a defined wavelength range, which light radiation, reflected from the surface to be inspected and detected by the sensor and/or by the camera, can be compared with a defined threshold value. This allows an evaluation of the degree of soiling, and generation and issuance of a soiling parameter. The determined values can also be displayed, by a comparison with threshold or boundary values, by a "traffic light display" on the flight attendant panel, e.g., green=clean, amber=inspect, red=critical soiling or odor. If required, as an alternative or in addition, the previously mentioned can also be acoustically displayed. It is also possible for the room to be closed to further use in the case of "red". For example, an output device for issuing a soiling parameter generated by the evaluation unit can be provided.

According to a third embodiment, a vehicle is provided with a vehicle structure and at least one cabin region arranged in the vehicle structure. The cabin region comprises at least one space unit according to any one of the above-mentioned exemplary embodiments with an inspection device according to any one of the above-mentioned embodiments.

According to another embodiment, the vehicle is i) an aircraft, ii) a bus coach, iii) a train coach and/or iv) a ship. In case of an aircraft, the vehicle structure is a fuselage structure in which the cabin region is provided. In case of other vehicles such as trains, busses and ships, a cabin region is provided in the vehicle's body structure and at least one space unit according to any one of the above-mentioned exemplary embodiments with an inspection device according to any one of the above-mentioned embodiments is provided in the cabin region.

According to a fourth embodiment, the use of an inspection device according to any one of the above-mentioned embodiments on board a vehicle, in particular on board an aircraft, is provided.

According to a further embodiment, the use of a space unit according to any one of the above-mentioned exemplary embodiments on board a vehicle, in particular on board an aircraft, is provided.

According to a fifth embodiment, a method is provided to monitor and assist in assuring hygienic conditions in a vehicle such as an aircraft. The method comprises the steps of: a) cleaning at least one surface to be cleaned on board a vehicle. The surface is irradiated by an optical detection device for rendering visible any soiling that, in visible light, is invisible to the human eye. The method further comprises: b) optically inspecting the quality of cleaning while the optical detection device is activated.

The surface to be inspected may include at least part of the floor surface. For example, cleaning in step a) may include at least partial cleaning of the surface to be cleaned.

The optical detection device may generate light that is invisible to the human eye, for example ultraviolet light (UV-light). The optical inspection in step b) can comprise a visual inspection. Furthermore, at the beginning of step a) the surface to be cleaned can be cleaned with visible room lighting activated.

In step a), it can further be provided for the surface at first to be cleaned with the visible room lighting activated and with the detection device deactivated, and subsequently to be cleaned with the visible room lighting deactivated and the detection device activated.

Following step b), it can be provided: c) evaluation of the cleaning process in step a) to be determined with reference to evaluation parameters that are determined in step b). For example, in step c) the visible room lighting is at least partially activated. This makes it possible, for example, to use more economical camera devices with average or below-average light sensitivity.

According to an embodiment, in step b) an optical sensor is provided, and light of a defined wavelength range, which light is reflected from the surface to be cleaned, is detected by the sensor so that a corresponding (measuring) signal can be generated. The reflected light is, for example, electromagnetic radiation in a wavelength range that is visible to the human eye, which radiation arises, for example, when UV light becomes visible because of fluorescence caused by soiling. For example, a detected light reflection can indicate soiling that has not yet been removed. The sensor can also detect invisible light that indicates soiling. Inspection by the sensor in step b) can take place with deactivated visible room lighting.

The (measuring) signal can be converted to an optical signal that is displayed as a signal for a cleaning process to be repeated. This can be, for example, in close proximity to the interior space to be cleaned, for example, in the region of an access door or at a central position, for example, at an operating element for the crew, for example the flight crew in an aircraft or the conductor team on board a train.

According to an embodiment, in step b) a camera is provided as a sensor, and, by image evaluation, spatial allocation of the soiling not yet removed takes place. Following step b), it is provided for soiling that has not yet been removed to be highlighted by visible marking.

The camera records, for example, at least one defined sub-region of the surface to be cleaned. For example, in the case of a toilet monument the region directly around a toilet bowl can be captured by the camera, as can the region of the toilet bowl itself. Further, it can be provided for the region up to the door to be captured by a camera in order to assure that any soiling spread by users via the soles of their shoes can reliably be detected and subsequently cleaned.

According to a sixth embodiment, a method is provided to monitor and assist in assuring hygienic conditions in a vehicle such as an aircraft. The method comprises the following steps: a) querying an occupation status of a space unit on board a vehicle; and b) activating an optical detection device to render visible any soiling that in visible light is invisible to the human eye, and irradiating a surface to be inspected. The method also comprises: c) detecting light radiation of a defined wavelength range, which light radiation is reflected from the surface to be inspected; d) evaluating the degree of soiling of the surface to be inspected by comparing the detected light radiation with at least one defined threshold value, and generating a soiling parameter; and e) issuing the soiling parameter.

The surface comprises, as mentioned above, at least a part of the floor region or floor surface. The space unit can be a toilet monument, and a toilet room with a toilet facility is provided as an interior space. For example, step a) comprises querying a locking unit of an access door and a movement sensor in the interior of the space unit. For example, the following steps b) to d) can be initiated when the if the locking unit d) is activated, i.e., if the door is unlocked and the movement sensor has not generated a movement signal for a defined period of time, for example over a period of time of 20 seconds. This assures that when the inspection takes place no user is present in the interior space, for example in a toilet space.

Provision exists for self-cleaning toilets or toilet lids, as well as self-closing toilet lids, to connect to the control device, and for them to activate if a soiled state is detected when there is no user in the space. Furthermore, it can be provided for step a) to be initiated only if previously the use of the space unit has been determined In other words, inspecting the hygiene conditions in the interior space only takes place after use that could cause soiling.

Determining the use can, for example, take place by querying the locking unit of an access door and/or a movement sensor in the interior of the space unit. It is, of course, possible for this purpose to fall back on already existing systems, which are, for example, provided, in the case of the toilet being in use, in order to provide a corresponding signal to other users, e.g., passengers in the cabin space. This also applies to the above-mentioned querying relating to the space occupation, which querying is not available for starting the inspection.

Furthermore, it can be provided that when a defined level of soiling is exceeded, i.e., when a defined value relating to the soiling parameter is exceeded, the toilet space is no longer available for use, but may be locked instead. In this way it can be assured that an excessively soiled toilet region or some other excessively soiled space region, for example a diaper-changing room, can no longer be entered by users so as to prevent soiling from being spread further afield, in particular into the cabin region.

Furthermore, it can be provided that when a defined level of soiling is exceeded, i.e., when a defined degree of soiling is exceeded during operation, e.g., flight operation, a cleaning process is activated. For example, an automatic cleaning process can be provided, e.g., by automatic application of a disinfectant, for example, in the form of a spray, and of a subsequently provided minimum period during which the space region cannot be used, to assure an adequate duration of action of the disinfectant. Moreover, the cleaning process can also take place manually or can be carried out by a combination of automatic steps with manual support.

After completion of cleaning, automatic inspection of the state of hygiene can be assured in that the method to assure hygienic conditions, as described above in various embodiments, is repeated, if desirable, at defined intervals.

The embodiments and aspects described above can be combined in various ways; in particular, it is also possible for aspects of the devices to be used for embodiments of the method as well as for the use of the device, and vice versa.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit application and uses. Furthermore, there is no intention to be bound by any theory presented in the preceding background or summary or the following detailed description.

Figure 1A:
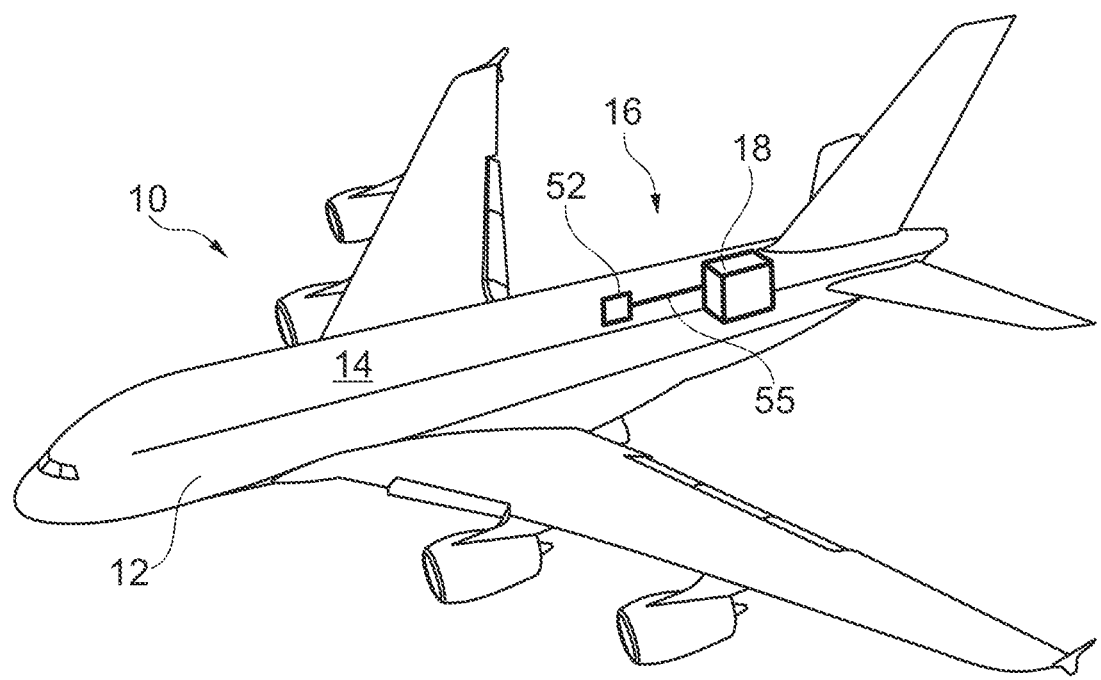
FIG. 1a is an aircraft as an example for a vehicle comprising a space unit and an inspection device according to an embodiment.

FIG. 1a shows an aircraft 10, as an example for a vehicle, comprising a fuselage structure 12 as a vehicle structure and at least one cabin region 14 arranged in the fuselage structure. It should be pointed out that the illustration is diagrammatic, and for reasons of clarity, for example, neither a cockpit region nor a cargo loading region is shown. The cabin region 14 comprises at least one space unit 16 that comprises an inspection device 18. For example, the space unit is a toilet monument, i.e. a space unit for use as a toilet, which space unit is separate from or partitioned within the cabin region 14. An embodiment also provides that the space unit 16 is, for example, a galley region (not shown in detail).

Figure 1B:
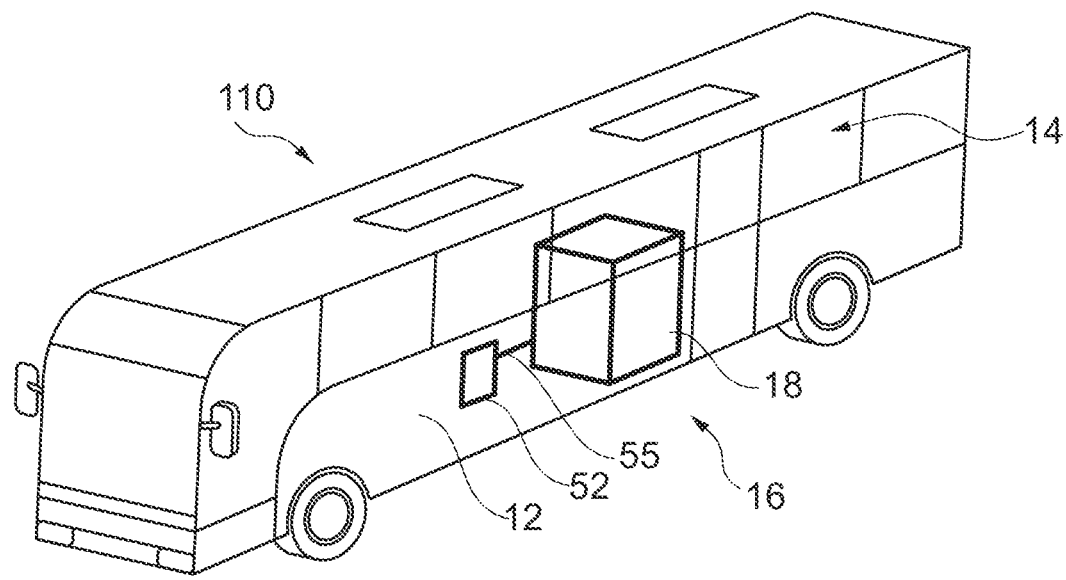
FIG. 1b is a bus as a further example for a vehicle comprising a space unit and an inspection device according to an embodiment.

FIG. 1b shows a bus or coach 110, as an example for a vehicle, comprising a vehicle structure 12 and a cabin region 14 arranged inside. The cabin region 14 comprises at least one space unit 16 that comprises an inspection device 18. For example, the space unit 16 is a toilet arrangement usable for the passengers on board while the bus is driving.

Figure 1C:
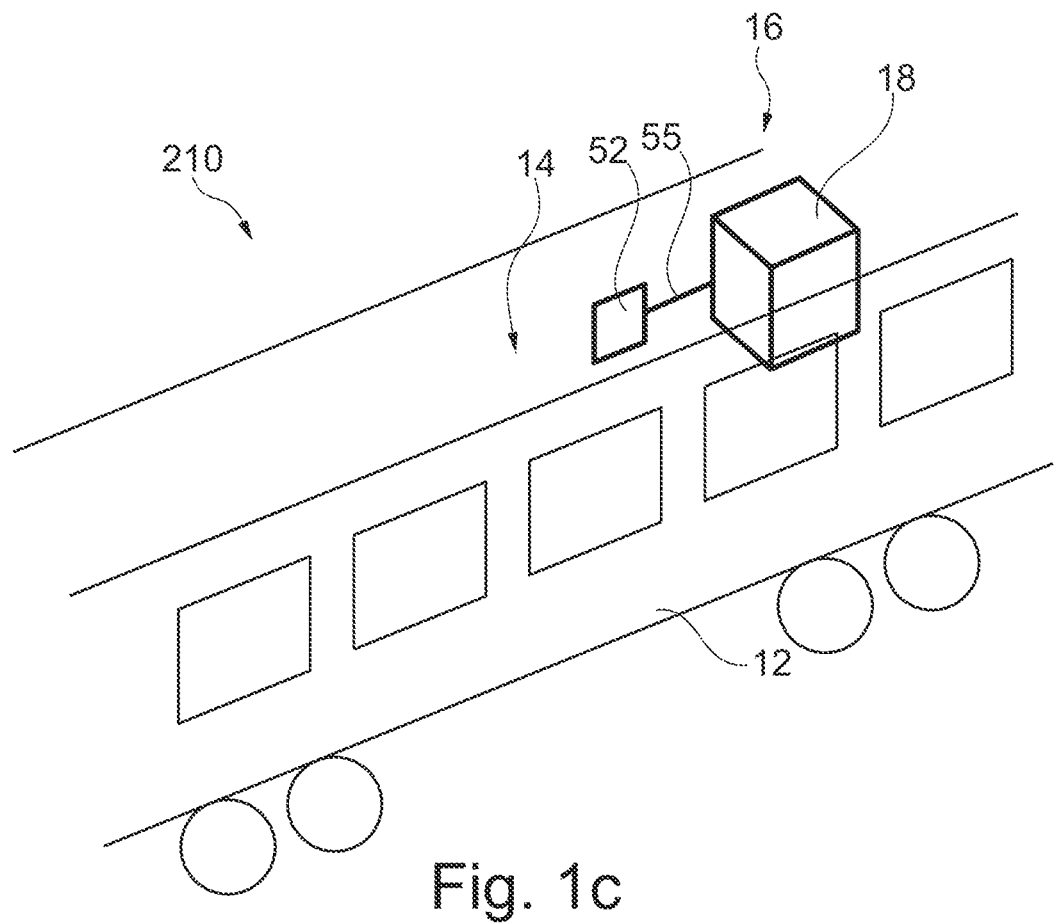
FIG. 1c is a train as a another example for a vehicle comprising a space unit and an inspection device according to an embodiment.

FIG. 1c shows a section of a train carriage 210, as an example for a vehicle, with, once again, a vehicle structure 12 and a cabin region 14 inside. The cabin region 14, for example also partially equipped with seating, comprises at least one space unit 16 that comprises an inspection device 18. For example, the space unit 16 is a toilet or a smaller passenger compartment, for example for passengers with small children.

Figure 1D:
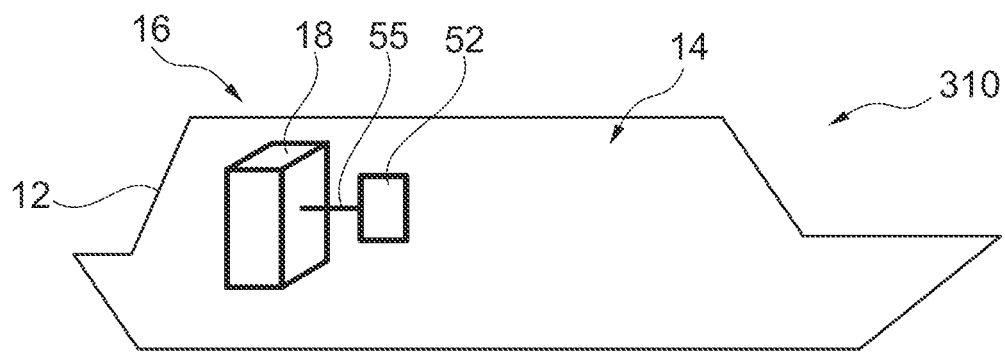
FIG. 1d is a ship as a still further example for a vehicle comprising a space unit and an inspection device according to an embodiment.

FIG. 1d very schematically shows a simplified boat or ship 310, as an example for a vehicle, having a boat- or vehicle structure 12 and a cabin region 14 inside. The cabin region 14 comprises one (or more) space unit(s) 16 including an inspection device 18. The space unit may be a restroom (sanitary room) or a room for passengers.

It is noted that the space unit 16 may be provided for passengers and/or for staff members of the respective vehicle. The space unit 16 may be arranged for the normal stay of the passenger while on board, such as the cabin with the seating in an aircraft, or for a temporal stay of passengers, such as bathrooms, etc. The space unit 16 may also be provided as a service room or other type of room for the staff/personnel, such as a kitchen or preparation area, or as a medical emergency space.

Figure 2:
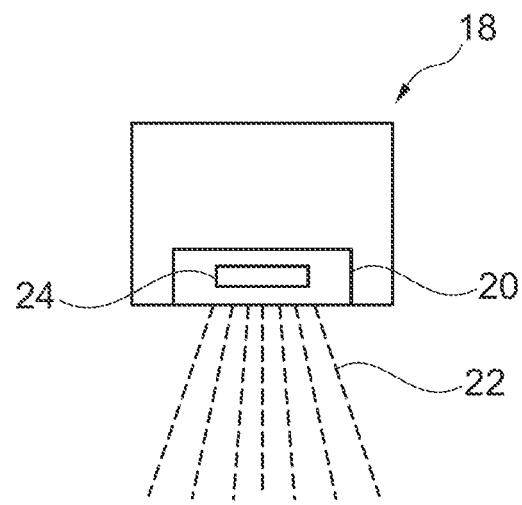
FIG. 2 is an inspection device to monitor hygienic conditions in interior spaces on board a vehicle according to an embodiment.

FIG. 2 shows in greater detail the inspection device 18 that is provided to assure hygienic conditions in interior spaces on board a vehicle, for example on board an aircraft, and that comprises an optical detection device 20. The optical detection device 20 generates electromagnetic radiation, which in FIG. 2 is diagrammatically indicated by fan-shaped lines 22, wherein this is a purely diagrammatic representation and is not to be interpreted as a limiting characteristic of the actual propagation of the electromagnetic radiation. The electromagnetic radiation is provided for irradiation of a surface to be cleaned; and it renders visible soiling that, in visible light, may be invisible to the human eye. In this context, the term "rendering visible" can relate to light that is rendered visible to the human eye, and/or rendered visible to sensors or detectors.

The optical detection device 20 is permanently installable on an interior lining. For example, the optical detection device 20 comprises a UV-light source 24. With ultraviolet radiation generated by a UV-light source, which radiation may at first be invisible to the human eye, fluorescence can be generated in certain substances. This, in turn, is visible to the human eye so that by the UV-radiation certain substances, in particular soiling, for example in the form of residual urine, which substances may otherwise be invisible to the human eye, can be rendered visible.

According to a further embodiment, instead of or in combination with UV radiation, other electromagnetic radiation may be used that renders visible such soiling. In other words, certain substances that in normal light, e.g., daylight, or in artificial light normally used in the cabin region (i.e., in visible light), remain invisible to the human eye. This is due to the fact that the substances are invisible or are present to such a small extent that the human eye cannot perceive them against the background, for example, the floor region or the wall region. An embodiment particularly provides for those substances to be detected by the inspection device, which substances negatively affect comfort, for example as a result of odor nuisance, as well as those soiling, for example secretion residues, that transmit pathogens, for example bacteria or viruses.

According to an embodiment, by the inspection device, on the one hand already during a cleaning process soiling is rendered visible so that it can be removed in a targeted manner, and subsequent to cleaning, reliable and safe inspection of the hygiene conditions in the interior space is assured. This is of importance, in particular, in the field of toilets or similar useable spaces, for example diaper-changing rooms.

Figure 3:
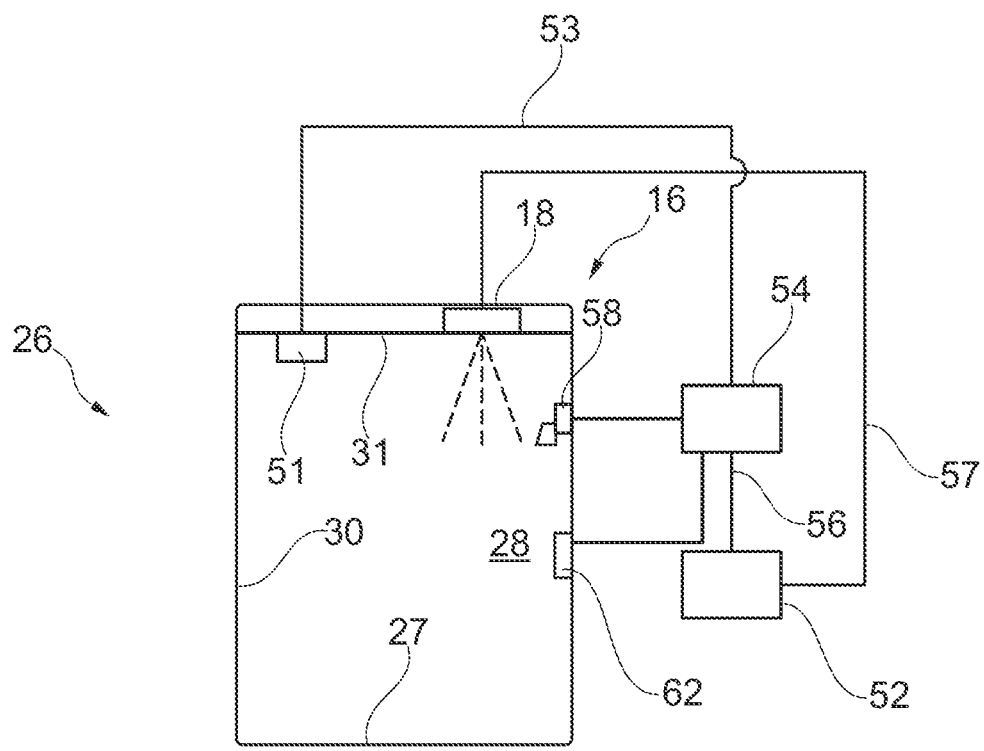
FIG. 3 is a space unit for a vehicle according to an embodiment.

FIG. 3 shows an embodiment of the space unit 16 for a vehicle, such as an aircraft, which space unit 16, has been mentioned in the context of FIG. 1a-d. The space unit 16 comprises an interior lining 26 and at least one inspection device 18, which has also already been mentioned. The interior lining 26 comprises a floor region 27 and a wall lining 30 that at least in part encloses an interior space 28. The inspection device 18 is designed and arranged in such a manner that at least part of the interior lining 26 can be irradiated by the optical detection device. According to a further embodiment, as an alternative or in addition, the inspection device 18 can be designed in such a manner that at least part of an interior structure and/or a utility zone in the interior of the space unit 16 can be irradiated by the optical detection device 20.

The above is to be explained in more detail with reference to the following examples in FIG. 4 and FIG. 5. It is expressly pointed out that the use of the space units shown in the figures is shown as an example, and that the embodiments also relate to other space units on board an aircraft or another type of vehicle.

Figure 4:
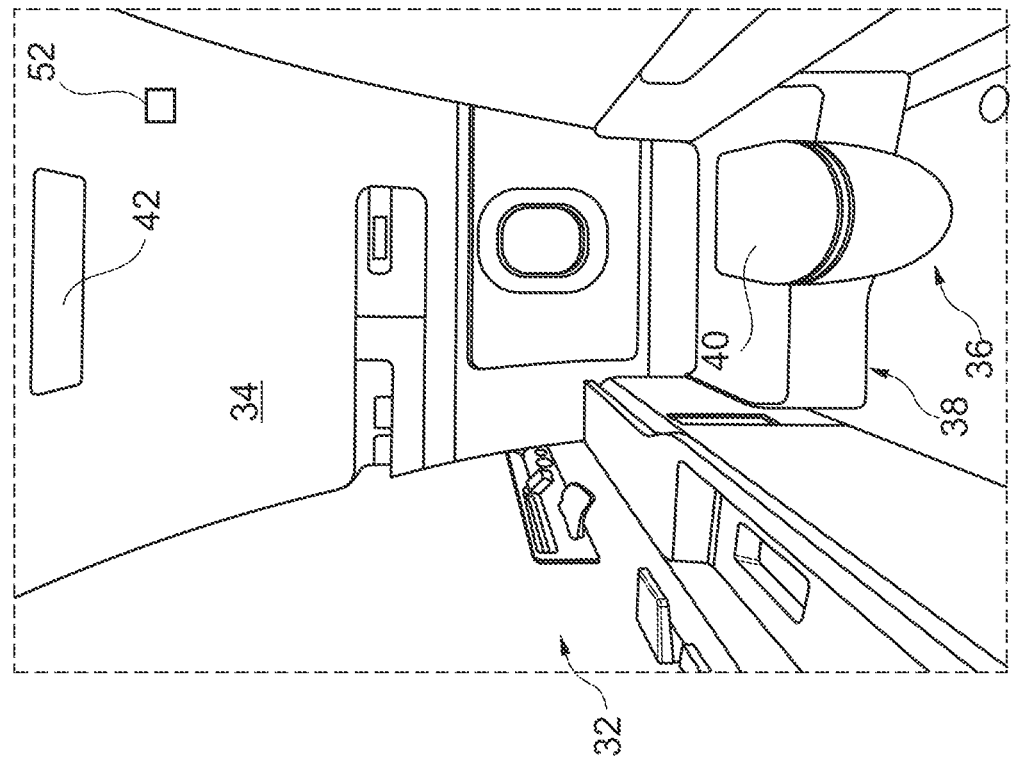
FIG. 4 is a further exemplary embodiment of the space unit.

FIG. 4 shows the space unit 16 as a toilet monument 32 which in FIG. 4 is shown in a perspective interior view. The interior 28 in FIG. 4 thus comprises a toilet space 34 equipped with a toilet facility 36. The inspection device 18 is designed in such a manner that at least part of the floor region, the interior lining, and/or the toilet facility can be irradiated by the optical detection device. The detection device can also be permanently mounted to other structures inside the interior space that are fixedly mounted (not further shown). FIG. 4 shows, for example, two optical detection devices. A first detection device 38 is arranged underneath an attachment region for a toilet 40, and a second detection device 42 is provided in the upper region of the wall lining in the transition to the ceiling surface. The detection devices 42 and 38 are, for example, UV-lamps, wherein the detection devices can be combined with interior lighting provided in the same position. The electrical connection of the detection device, in particular of a UV-lamp, can take place in a manner that is analogous to that of the remaining lighting. Depending on the type of vehicle, controlling can, for example, take place by way of a dedicated controller, for example a monument controller in an aircraft, or the controller of a device installed in the toilet segment or in the toilet monument. The optical detection device or the several optical detection devices can be designed so that they are not readily visible to the user using the toilet facility. Of course, instead of the two optical detection devices shown, it is also possible for only one optical detection device or for several optical detection devices to be provided.

Figure 5:
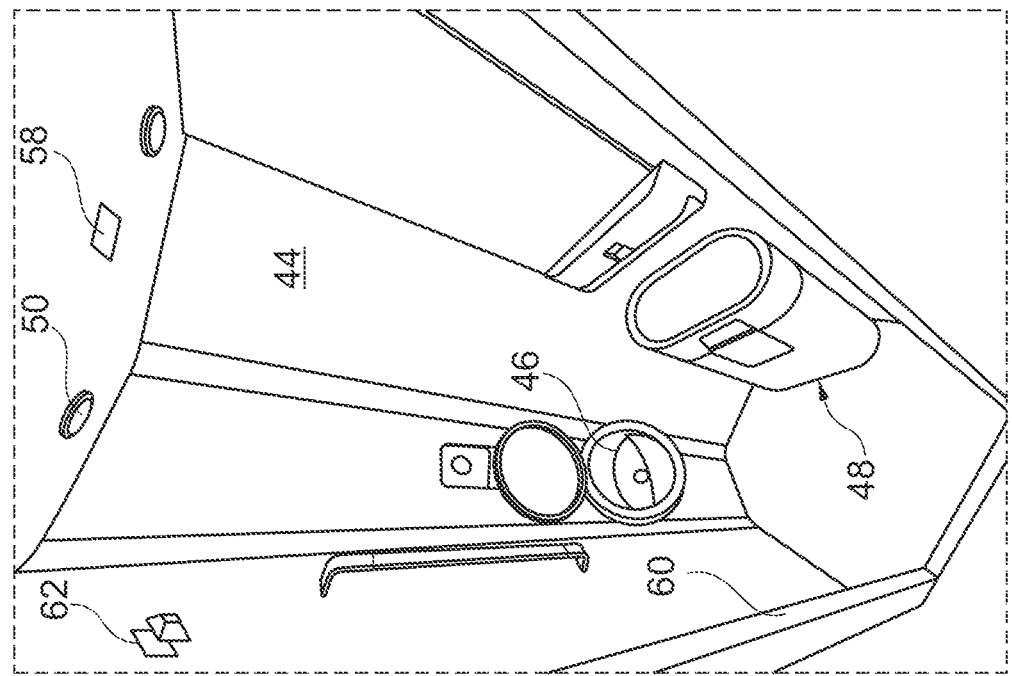
FIG. 5 is a further exemplary embodiment of the space unit.

FIG. 5 as a further example shows an interior toilet space 44 that comprises a urinal 46 instead of a toilet 40. In this use, too, one or several optical detection devices can be provided, for example a first detection device 48 underneath a washbasin structure, and a second, optical, detection device 50 in the region of the ceiling segment. Here again, of course, only one optical detection device or, alternatively, several optical detection devices can be provided. The detection devices are designed to integrate into the ceiling structure with the ceiling lighting that is already provided in that region. The detection device 48, which has been provided underneath the washbasin, may also be invisible to the user.

According to a further embodiment, which is diagrammatically indicated in FIG. 1a-d and is also diagrammatically shown in FIG. 3, but is not shown in detail in FIG. 4 and FIG. 5, the inspection device may be controllable from outside the space unit. In other words, the inspection device can be activated and deactivated from outside the space unit. For example, activated and deactivated by way of a flight attendant panel or service personnel control board, which is diagrammatically indicated in FIG. 1a-d and FIG. 3 by reference character 52 that refers to a rectangle, which is connected to the space unit 16 by way of a connecting line 55. The connecting line 55 shown is, of course, a diagrammatic indication of the connection, which can be designed, for example, so as to be wired or wireless, and, in particular, can also be provided by way of a bus system for controlling the electrical components of a space unit, for example of a toilet monument.

However, the external controllability, and thus the respective features of the control board 52 and the connecting line 55 shown in the general overview drawings of FIGS. 1a-d, is not shown in detail, and thus described as an option. In other words, the respective inspection devices 18, and also the space units 16, may also be provided without such external controllability.

According to a further embodiment, the inspection device can comprise a sensor 51, which is an optical sensor, which detects light of a defined wave range, which light is reflected from the surface to be cleaned, and can generate a corresponding (measuring) signal. For example, the sensor 51 can be arranged in the upper wall region or ceiling region and can be aligned in such a manner that it covers in particular the critical surfaces. In particular, the floor and the region of the toilet 40 or of the urinal, as well as the wall region situated directly underneath and beside the previously mentioned, as well as a floor region (not shown in detail) in front of a door opening.

The sensor 51 is also shown diagrammatically in FIG. 3. A connection 53 to a processing unit 54 can be provided in which further signal processing takes place. For example, a signal that indicates soiling can be generated, which is indicated by a connecting line 56, and the signal can be transmitted to the control board 52 in order to, in that location, point out soiling, for example as a visual message or as an acoustic signal.

According to a further embodiment, in the region of the interior space a camera 58 can be provided which is also shown in FIG. 3 and also in FIG. 5. The camera 58 can be provided instead of, or in addition to, the sensor 51 and, by way of a data link by image evaluation, for example in the control unit 54, can make it possible to achieve spatial allocation (e.g., the location) of not yet removed soiling. Subsequently, with the use of a marking, for example in the form of controllable ceiling lighting elements, the not yet removed soiling can be highlighted by visible marking, which is not, however, shown in detail.

According to a further embodiment, devices for querying an occupation status of the space unit can be provided, for example, a query device of a locking unit (not shown in detail) of an access door whose door frame is diagrammatically indicated in FIG. 5 and comprises the reference character 60. Furthermore, a movement sensor 62 can be provided that determines movements in the interior space.

The locking unit query and the movement sensor can also be connected to a control unit, for example, to the control unit 54 in FIG. 3; they make it possible to inspect the state of hygiene with defined parameters, for example after use of a toilet monument (fixture). It may be assured that the hygiene inspection takes place only if no user is present within the toilet space.

By the already mentioned sensor or also the already mentioned camera device it is, furthermore, possible to detect the reflected light radiation of a defined wavelength range and to carry out evaluation of the degree of soiling of the surface to be inspected. To this effect the detected light radiation can be compared with a defined threshold value and if the threshold value is exceeded, a corresponding signal can be generated. Comparing the detected light radiation with the defined threshold value may also be used to generate a soiling parameter or a value relating thereto, which value can also be made available. For example, an evaluation unit can be provided which, together with the image data furnished by the camera device, can differentiate, for example, between urine soiling and toilet paper lying around.

Figure 6:
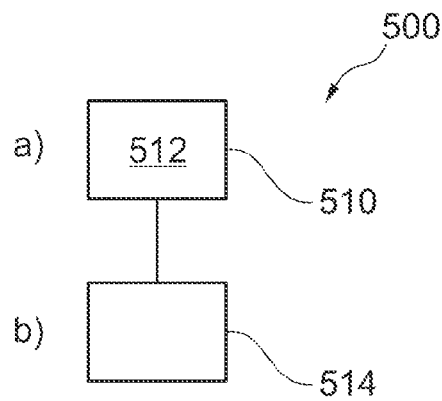
FIG. 6 shows steps of a method to monitor hygienic conditions in a vehicle according to an embodiment.
Figure 7:
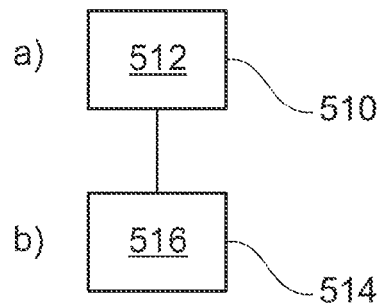
FIG. 7 is a further embodiment of a method to monitor hygienic conditions in a vehicle.

With reference to the following FIG. 6 to FIG. 17, several embodiments of a method to assure hygienic conditions in a vehicle such as an aircraft, train or bus or ship, will be discussed. FIG. 6 shows a method 500 to monitor and/or assure hygienic conditions in a vehicle. The method includes: in a cleaning step 510, at least one surface to be cleaned on board a vehicle is cleaned, wherein the surface is irradiated 512 by an optical detection device for rendering visible any soiling that in visible light is invisible to the human eye. Subsequently, in a control step 514, visual inspection of the quality of cleaning is carried out, for example while the optical detection device is activated.

The surface to be cleaned comprises at least a part of the floor area or floor region. The cleaning step 510 can also be referred to as step a), and the inspection step 514 can be referred to as step b). The optical detection device generates, for example, ultraviolet light. According to a further example, shown in FIG. 7, the optical inspection 514 in step b) comprises a visual inspection 516.

Figure 8:
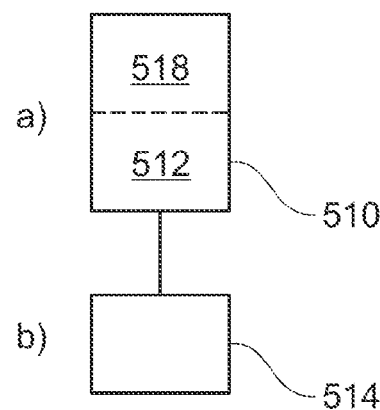
FIGS. 8-17 show further embodiments of methods to monitor hygienic conditions in a vehicle.

According to a further example, shown in FIG. 8, at the beginning of step a) it is provided for the to-be-cleaned-surface to be cleaned with the visible room lighting activated, which is indicated by the reference character 518. This is followed by the cleaning with the optical detection device 512 activated.

Figure 9:
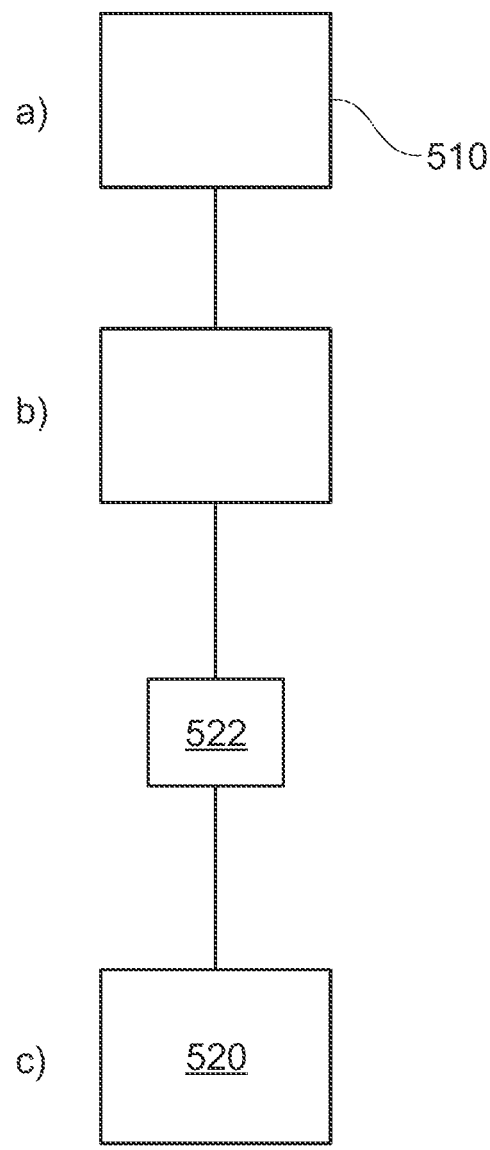

According to a further example, shown in FIG. 9, following step b) a step c) is provided in which an evaluation 520 of the cleaning step 510 in step a) takes place, for which purpose at first evaluation parameters 522 are generated, which may be determined in step b).

Figure 10:
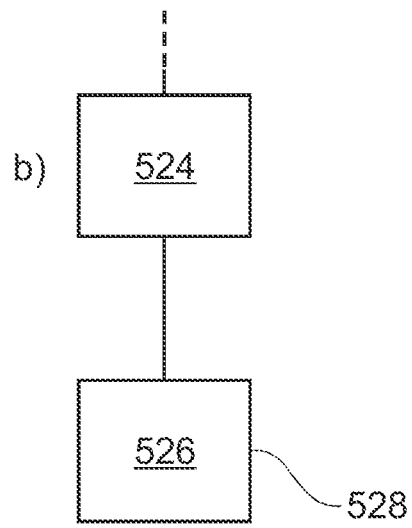

With reference to FIG. 10, for example in step b), an optical sensor can be provided, such that light of a defined wavelength range is reflected from the surface to be cleaned, is detected by the sensor, which is indicated by reference character 524, in order to subsequently generate a corresponding (measuring) signal 526, which is indicated by reference character 528.

Figure 11:
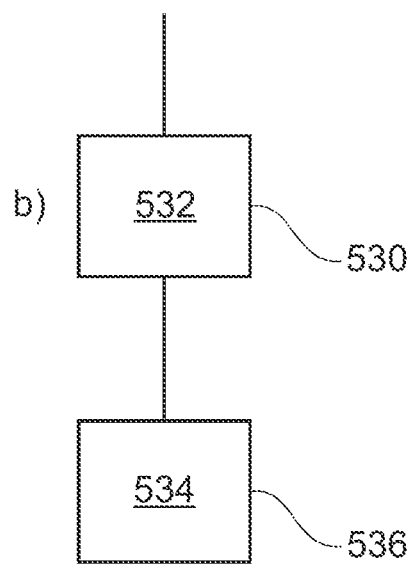

According to a further example, shown in FIG. 11, in step b) a camera can be provided as a sensor, and by an image evaluation process 530 a spatial allocation (e.g., location identification) 532 of any soiling that has not yet been removed can take place. Subsequent to step b) it can be provided for any soiling that has not yet been removed to be highlighted 536, for example by visible marking 534.

Figure 12:
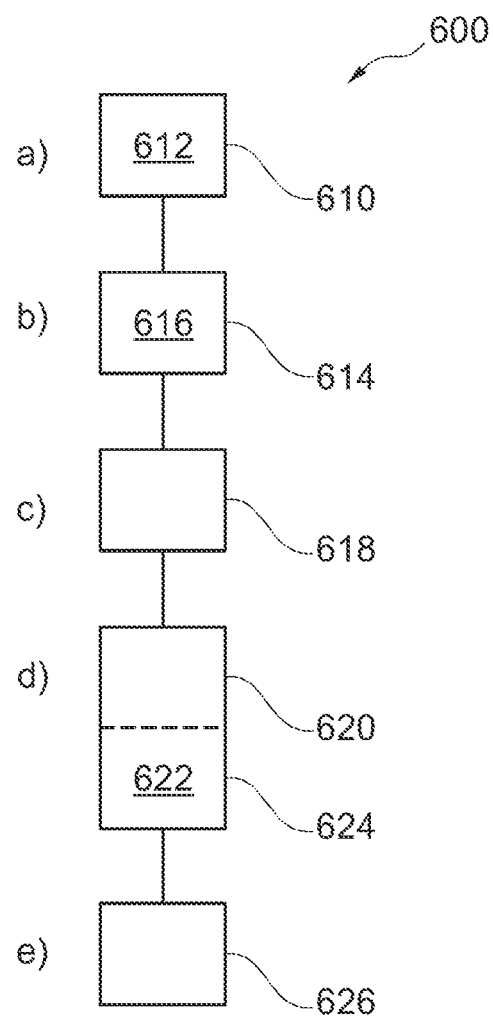

FIG. 12 shows a further method 600 that is also used to monitor hygienic conditions in a vehicle, e.g., an aircraft, and that comprises the following steps: in a query step 610 an occupation status 612 of a space unit on board a vehicle, for example, an aircraft, is queried. In an activation step 614 an optical detection device for rendering visible any soiling that in visible light is invisible to the human eye is activated, and irradiation 616 of a surface to be inspected takes place. This is followed by detection 618 of light radiation of a defined wavelength range, which light radiation is reflected from the surface to be inspected. Thereafter, an evaluation step 620 is provided in which the degree of soiling of the surface to be inspected is determined or ascertained by comparing the detected light radiation with at least one defined threshold value, and a soiling parameter 622 is generated.

Subsequently, issuing 626 the soiling parameter is provided, for example, as a numerical value or as an indicator on a soiling diagram. The soiling parameter can also be represented as code in an area plan of the vehicle, e.g., an aircraft, bus, train or ship, in order to provide an improved overview of the quality of cleaning or of the hygiene conditions of the individual surface segments.

Figure 13:
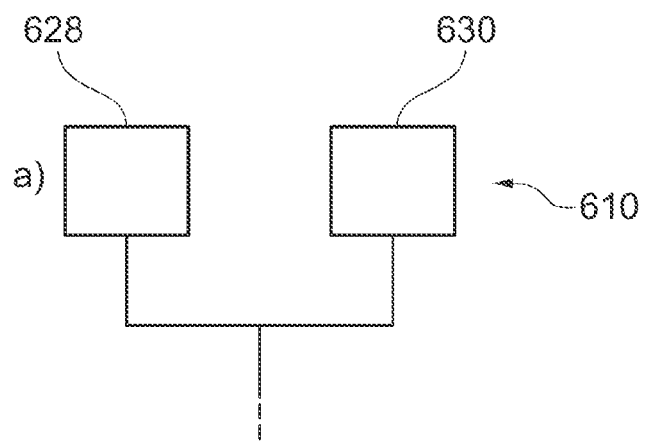
Figure 14:
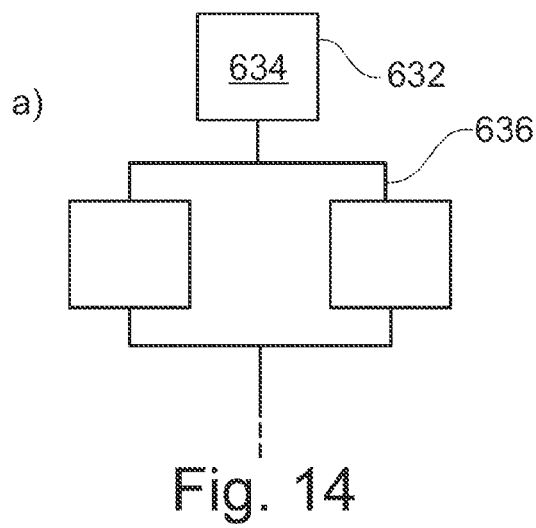

The query step 610 can also be referred to as step a), the activation step 614 as step b), the acquisition step 618 as step c), the evaluation step 620 as step d), and the output step 626 as step e). In step a), the querying 610 can, for example, comprise querying 628 a locking unit of an access door and querying 630 a movement sensor in the interior space of the space unit, which is shown in FIG. 13. For example, step a) is typically initiated only if previously in an acquisition step 632 the use 634 of the space unit has been determined, wherein initiating is diagrammatically indicated in FIG. 14 by a branching part 636.

Figure 15:
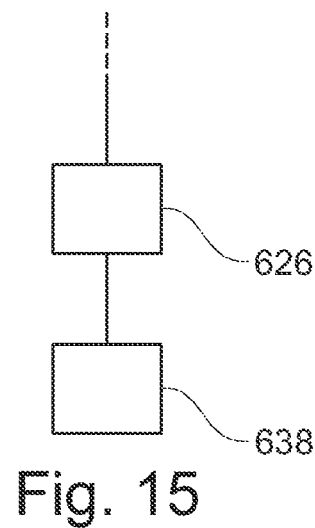
Figure 16:
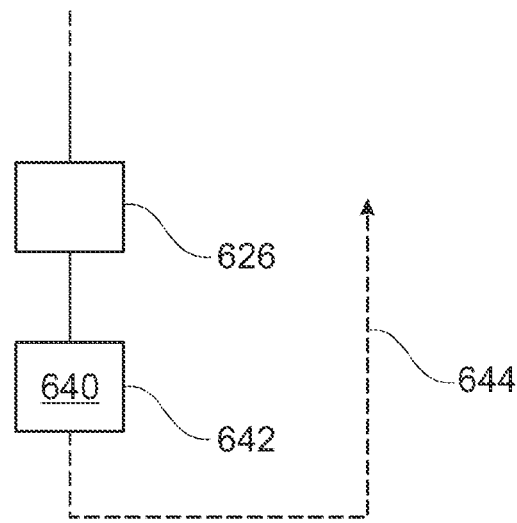

Furthermore, it can be provided for the interior space, in particular a toilet space, to be no longer available for use and to be locked if a defined degree of soiling has been exceeded, i.e. if a value relating to the soiling parameter has been exceeded, with such locking being indicated in FIG. 15 by reference character 638. Furthermore, it can be provided that if a defined degree of soiling has been exceeded, a cleaning process 640 is activated 642, which, in particular, can also be provided during, for example, flight operations. This takes place depending on the respective flight conditions at the time, and can be prevented, in particular, during the take-off and landing phases as well as in flight sectors where turbulence is experienced. Activation 642 is shown in FIG. 16.

According to a further example, the described method in the various embodiments can also be carried out repeatedly, in particular determining the respective degree of soiling at a given time. This repeated implementation is diagrammatically indicated in FIG. 16 by a dashed arrow 644, but is also intended in relation to other examples. It should be pointed out that the individual examples and aspects of the method are also provided in different combinations which, however, are no longer described and shown.

Figure 17:
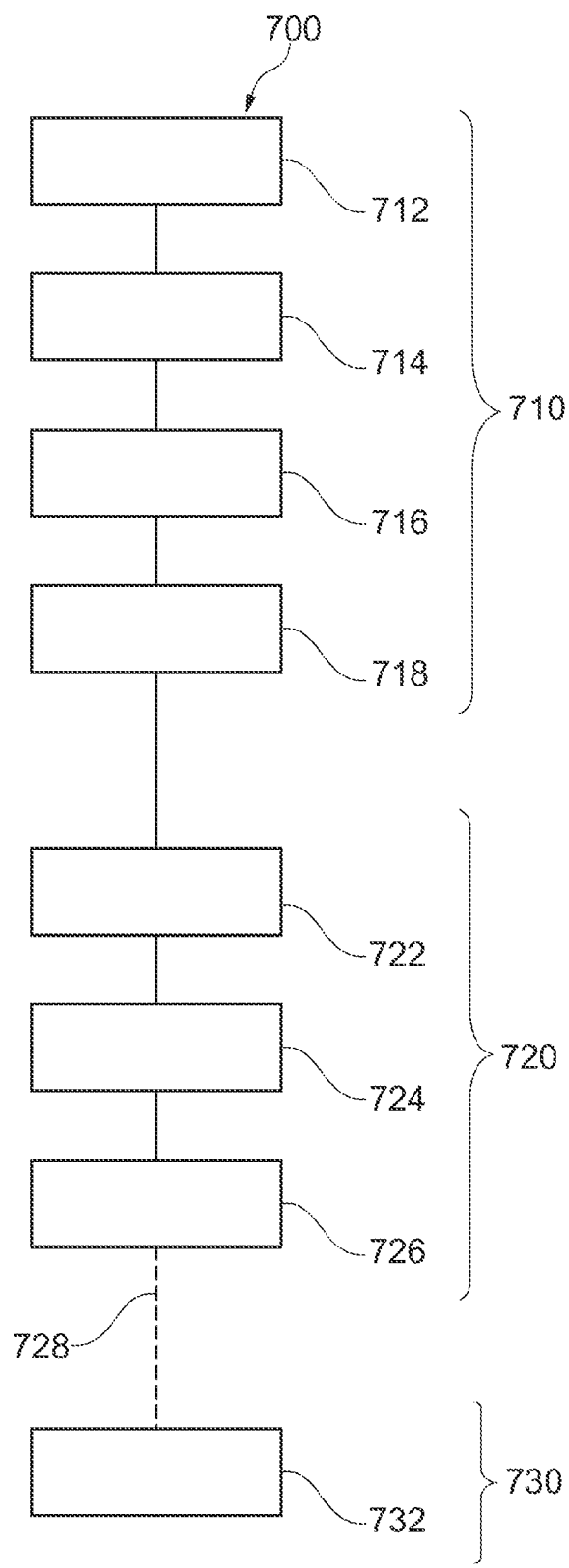

In FIG. 17 an exemplary sequence of an optimized cleaning process 700 with hygiene inspection of a toilet monument on board a vehicle, in particular on board an aircraft, is described. In a first part 710, firstly cleaning 712 of heavy soiling in the toilet monument with standard lighting is provided. This is followed by activation 714 of a toilet monument hygiene inspection according to an embodiment on an operating element for staff or service members, such as flight attendants. Subsequently, partial cleaning 716 of the toilet monument takes place by disclosing any invisible soiling by the inspection device, which has already been described in detail, with an optical detection device, which devices can also be referred to as a toilet-monument hygiene inspection device. This is followed by deactivation 718 of the toilet-monument hygiene inspection on the operating element for the staff, for example flight attendants.

In a second part 720, at first activation 722 of the toilet-monument hygiene inspection on, for example, the flight attendant panel, or other type of interface or control device, is provided. This is followed by a visual inspection 724 of the quality of the cleaning of the toilet monument. Subsequently, deactivation 726 of the toilet-monument hygiene inspection on the flight attendant panel (control panel) takes place. Optionally, subsequently a third part 730 can be provided, in which evaluation 732 of the cleaning process, and in particular of cleaning personnel, is provided to assure that the vehicle operator's hygiene standards are met. This in turn can also be used as the basis for evaluating the price/performance ratio of cleaning, which as a rule is purchased from third-party companies as a service.

According to the embodiments, it is possible to inspect the hygiene conditions in the interior of space units in an aircraft, or other vehicle, in particular for toilet monuments, which are also referred to as lavatories, and to improve the cleaning process itself. As a general rule, lavatories are heavily soiled at the end of a flight. The cleaning teams at the airport generally have very small time-windows during which to clean the lavatories. Therefore, the inspection device is used to assure hygienic conditions according to the embodiments as well as the space units according to the embodiments for an aircraft. The embodiments are also used for improved utilization of the available time window. Similar is the case for other vehicles, which are cleaned during stops or other pauses of travelling. However, also cleaning during the use of the vehicle, such as for trains or ships, is a time relevant procedure since the cleaning prevents the use of the space. Even if obvious soiling, i.e., dirt that is visible to the naked eye, can usually be removed quickly, often, incomplete cleaning processes result, in particular, in soiling that while not being visible nevertheless as a rule causes an odor nuisance. Because of the optical detection device according to the embodiments it is possible to render visible to cleaning personnel also such invisible soiling, in particular urine residues, and furthermore to provide a reliable inspection relating to the cleaning performed. This is, in particular, advantageous if, in the future, urinals are increasingly used in aircrafts, for example, in particular if several urinals are installed in a toilet region or in a toilet space.

Since according to some embodiments it is provided for the inspection device with the optical detection device to be permanently installed, reliable cleaning is possible at any time, as is a reliable inspection thereof, which also can be used to inspect the hygiene conditions during the use, i.e., during the flight. Even if permanent installation of the inspection device according to the embodiments entails additional expenditure, and in particular an increase in weight, the savings or the increase in quality, and thus assuring that increased demands for hygiene are met. In addition, the embodiments are advantageous for economic reasons to such an extent that the disadvantages described above, in particular also the installation expenditure and the installation space needed, in addition to the aspect of increased weight, are to be considered as being secondary.

In addition, it should be pointed out that "comprising" does not necessarily exclude other elements or steps, and "a" or "one" does not exclude a plural number. Furthermore, it should be pointed out that characteristics or steps which have been described with reference to one of the above exemplary embodiments and aspects can also be used in combination with other characteristics or steps of other exemplary embodiments and aspects described above. Moreover, while at least one exemplary embodiment has been presented in the foregoing summary and detailed description, it should be appreciated that a vast number of variations exist. It should also be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalents.

What is claimed is:

1. A space unit for a vehicle, comprising:
    an interior lining that comprises a floor region and a wall lining that at least partially encloses an interior space;
    an inspection device to monitor hygienic conditions in an interior of the vehicle including an optical detection device that is configured to:
        generate electromagnetic radiation to temporarily irradiate at least part of the floor region;
        render visible a soiling on the floor region, which in visible light is invisible to a human eye; and
        permanently arranged such that the at least part of the floor region is temporarily irradiated by the optical detection device to render visible the soiling on the floor region that, in the visible light, is invisible to the human eye; and
    a control unit in communication with the optical detection device that activates the optical detection device to irradiate the at least part of the floor region if the space unit is unoccupied.

2. The space unit of claim 1, wherein the optical detection device comprises at least one UV-light source.

3. The space unit of claim 1, wherein the inspection device is arranged such that a part of the wall lining is temporarily irradiated by the optical detection device to render visible the soiling on the wall lining that, in the visible light, is invisible to the human eye.

4. The space unit of claim 1, wherein:
    the space unit is a toilet unit;
    the interior space is a toilet space with a toilet facility, and
    the inspection device is arranged such that at least a part of the toilet facility can be irradiated by the optical detection device.

5. The space unit of claim 1, further comprising an optical sensor that is configured to detect a light of a defined wavelength range, which is a reflected light, by which a corresponding signal can be generated.

6. The space unit of claim 1, further comprising:
    a camera configured to detect light of a defined wavelength range reflected from a surface to be cleaned;
    an evaluation unit configured such that by image evaluation, soiling that has not yet been removed can be spatially allocated; and
    a marking configured such that soiling not yet removed can be highlighted with a visible identifier.

7. A space unit for a vehicle, comprising:
    an interior lining that comprises a floor region and a wall lining that at least partially encloses an interior space;
    an inspection device to monitor hygienic conditions in an interior of the vehicle including an optical detection device that is configured to:
        generate electromagnetic radiation to temporarily irradiate at least part of the floor region;
        render visible a soiling on the floor region, which in visible light is invisible to a human eye; and
        permanently arranged such that the at least part of the floor region is temporarily irradiated by the optical detection device to render visible the soiling on the floor region that, in the visible light, is invisible to the human eye;
    an optical sensor that is configured to detect a light of a defined wavelength range, which is a reflected light, by which a corresponding signal can be generated;
    a query device configured to detect an occupation status of the space unit on board the vehicle; and
    a control unit configured to:
        activate the optical detection device when the space unit is not occupied in order to irradiate a surface to be inspected;
        compare a light radiation of the defined wavelength range, which is reflected from the surface to be inspected, with a defined threshold value in order to evaluate the degree of soiling; and
        generate a soiling parameter.

8. A vehicle comprising:
    a vehicle structure;
    a cabin region arranged in the vehicle structure;
    at least one space unit of the cabin region with an inspection device and a control unit in communication with the inspection device, the inspection device comprising an optical detection device that is configured to:

generate electromagnetic radiation to irradiate a cleaning surface within the at least one space unit;

render visible soiling, which in visible light is invisible to a human eye; and be permanently installed on an interior lining of the at least one space unit of the cabin region, wherein the control unit activates the optical detection device to irradiate the cleaning surface when the at least one space unit is not occupied.

9. The vehicle according to claim 8, wherein the vehicle is an aircraft.

10. The vehicle according to claim 8, wherein the vehicle is a bus coach.

11. The vehicle according to claim 8, wherein the vehicle is a train coach.

12. The vehicle according to claim 8, wherein the vehicle is a ship.

13. A method to monitor hygienic conditions in a vehicle, comprising:

cleaning a surface to be cleaned on board the vehicle, the surface contained within a space unit of the vehicle;

irradiating the surface with an optical detection device for rendering visible a soiling that, in visible light, is invisible to a human eye, if the space unit is unoccupied; and optically inspecting the quality of cleaning while the optical detection device is irradiating the surface.

14. The method of claim 13, wherein the optically inspecting the quality of cleaning comprises:

detecting a light of a defined wavelength range, which is reflected from the surface with an optical sensor; and generating a corresponding signal.

15. The method of claim 13, wherein the optically inspecting the quality of cleaning comprises:

evaluating an image taken by a camera in order to spatially allocate non-removed soiling; and highlighting the non-removed soiling with a visible marking.

16. A method to monitor hygienic conditions in a vehicle, comprising:

querying an occupation status of a space unit on board the vehicle;

activating an optical detection device to render visible any soiling that, in visible light, is invisible to a human eye;

irradiating an inspection surface;

detecting a light radiation of a defined wavelength range that is reflected from the inspection surface;

evaluating a degree of soiling of the inspection surface by comparing the light radiation with at least one defined threshold value;

generating a soiling parameter based at least in part on the evaluating the degree of soiling; and issuing the soiling parameter.

\* \* \* \* \*